United States Patent
Park et al.

(10) Patent No.: US 12,061,203 B2
(45) Date of Patent: Aug. 13, 2024

(54) FLUORESCENT COMPOUND WITH CYANURIC-HYDROXIDE AND PREPARATION METHOD THEREOF

(71) Applicant: Bioacts Corporation, Incheon (KR)

(72) Inventors: Jin Woo Park, Incheon (KR); Kiwon Kim, Incheon (KR); Gyeong Rim Shin, Incheon (KR); Eunseo Yu, Incheon (KR)

(*) Notice: Subject to any disclaimer, the term of this patent is extended or adjusted under 35 U.S.C. 154(b) by 0 days.

(21) Appl. No.: 17/536,035

(22) Filed: Nov. 28, 2021

(65) Prior Publication Data

US 2022/0229063 A1    Jul. 21, 2022

(30) Foreign Application Priority Data

Jan. 18, 2021 (KR) .................. 10-2021-0006771

(51) Int. Cl.
| | | |
|---|---|---|
| C09B 23/06 | (2006.01) | |
| C09B 23/08 | (2006.01) | |
| C09B 23/10 | (2006.01) | |
| G01N 33/58 | (2006.01) | |

(52) U.S. Cl.
CPC ............ *G01N 33/582* (2013.01); *C09B 23/06* (2013.01); *C09B 23/083* (2013.01); *C09B 23/107* (2013.01)

(58) Field of Classification Search
CPC ...... C09B 23/107; C09B 23/083; C09B 23/06
See application file for complete search history.

(56) References Cited

U.S. PATENT DOCUMENTS

2016/0018389 A1* 1/2016 Koide .................. C07D 413/08
548/405

OTHER PUBLICATIONS

Agrawalla, et al. Bioconjugate Chemistry (2018), 29(1), 29-34; Accession No. 2017:1955427, retrived from STN.*
Chattaraj, et al. ACS Applied Materials & Interfaces (2016), 8(1), 802-808; Accession No. 2016:32007, retrieved from STN.*

* cited by examiner

*Primary Examiner* — Shawquia Jackson

(57) ABSTRACT

A fluorescent compound in accordance with exemplary embodiments of the present invention has high stability under a water-soluble condition to be easily stored for a long time and improve pH stability and can be more efficiently used for labeling and dyeing of a target material by introducing the triazine substituted with a hydroxyl group as a linker to improve the fluorescent intensity even at a low concentration as compared with the conventional structure. Further, the fluorescent compound is excellent in optical stability and exhibits stable fluorescence in long-term dyeing, and is excellent in fluorescence intensity while being not accumulated in the body, and thus, can be easily dyed and imaged in vivo even in the use of a small amount as compared with the conventional dyes to be economically used.

6 Claims, 1 Drawing Sheet

|  | Compound 2-2 | Compound 2-2(1/2) | Compound 2-2(1/4) |
|---|---|---|---|
| $PL_{max}$ (nm) | 667 | 666 | 663 |
| PL Intensity | 589.529396 | 302.123543 | 158.08654 |
|  | Compound 2-1 | Compound 2-1(1/2) | Compound 2-1(1/4) |
| $PL_{max}$ (nm) | 656 | 655.5 | 652 |
| PL Intensity | 363.796975 | 187.233717 | 130.936134 |

FLUORESCENT COMPOUND WITH CYANURIC-HYDROXIDE AND PREPARATION METHOD THEREOF

CROSS-REFERENCE TO RELATED APPLICATIONS

This application claims priority to and the benefits of Korean Patent Application No. 10-2021-0006771 filed on Jan. 18, 2021, which is incorporated herein by reference in its entirety.

BACKGROUND

Field

The present disclosure relates to a fluorescent compound, which is a compound that is useful for a fluorescent diagnosis composition capable of prediction, diagnosis, treatment and prognosis of diseases.

The fluorescent compound provided in exemplary embodiments of the present invention relates to a fluorescent compound which improves that the fluorescence efficiency of conventional cyanine compounds is not high and comprises a triazine structure having a hydroxyl group substituted to a cyanine-based substituent as a linker.

The fluorescent compound provided in exemplary embodiments of the present invention has less noise and high fluorescent efficiency to improve the efficiency of a fluorescent signal when a desired biomaterial is detected using a fluorescence diagnostic composition of the present invention and thus can more accurately diagnose the biomaterial than the related art.

Description of the Related Art

Since a biomaterial itself has weak fluorescence or no fluorescence in visible and near-infrared regions, in a bio field, in order to observe biological phenomena at cellular and subcellular levels in vivo or in vitro or to make images and obtain optical images of a diseased area by being projected into a living body, imaging data have been obtained through a variety of methods using a fluorescent dye or a specific biomaterial pre-labeled with the fluorescent dye in the biomaterial with optical equipment.

Various optical analysis devices used in the bio field select a fluorescent dye with an excitation wavelength and an emission wavelength suitable for observing fluorescence according to embedded light sources and filters as a basic material or reagent.

In general, most of fluorescent dyes used for labeling biomolecules such as proteins or peptides include structures, such as anthranilate, 1-alkylthic isoindoles, pyrrolinones, bimanes, benzoxazole, benzimidazole, benzofurazan, naphthalenes, coumarins, cyanine, stilbenes, carbazoles, phenanthridine, anthracenes, bodipy, fluoresceins, eosins, rhodamines, pyrenes, chrysenes and acridines.

When selecting a fluorescent dye structure usable in the bio field from a plurality of fluorescent chromophores illustrated above, generally, it is important to emit strong fluorescence when most of biomolecules exist in a medium, that is, an aqueous solution and an aqueous buffer, and to have excitation and fluorescence wavelengths suitable for fluorescence equipment.

Dyes that may be mainly applied in the bio field need to preferably have less photobleaching and quenching in aqueous or hydrophilic conditions, to have a large molecular extinction coefficient so as to absorb a large amount of light, to be in the visible or near-infrared region of 500 nm or more far from the fluorescence range of the biomolecule itself, and to be stable under various pH conditions. However, structures of dyes usable for labeling biomolecules capable of satisfying the limitations are limited.

Fluorescent chromogens that meet these requirements include cyanine, rhodamine, flocseine, bodipy, coumarin, acridine, and pyren derivatives, and introduce functional groups so as to bind to a dye alone or a specific substituent in a biomolecular structure. Among them, xanthane-based flocseine and rhodamine, and polymethine-based cyanine derivative dye compounds are mainly commercialized.

In particular, the dye compound having the cyanine chromophore has an advantage that it is easy to synthesize compounds various absorption/excitation wavelengths. In addition, generally, since the dye compound having the cyanine chromophore is excellent in optical and pH stability, has narrow absorption and emission wavelength ranges, and has a fluorescent area of 500 to 800 nm, the dye compound is not overlapped with the self-fluorescent region of the biomolecule to be easily analyzed and has a slight difference according to a solvent and solubility characteristics, but has many advantages such as representing high molar adsorption coefficient, and thus is frequently used for biological applications.

In addition, the dye compound having the cyanine chromophore may also be usefully used for optical filters for image display devices or resin compositions for laser fusion. The compound having a large intensity of absorption in specific light has been widely used as an optical element of an optical filter for an image display device such as a liquid crystal display device, a plasma display panel, an electroluminescence display, a cathode tube display panel, and a fluorescent display tube or an optical recording medium of DVD±R and the like. The optical filter has required a function of selectively absorbing light having unnecessary wavelengths, and simultaneously has required light absorption of wavelengths of 480 to 500 nm and 540 to 560 nm to prevent reflections or glare of external light such as fluorescent light, and has required a function of selectively absorbing wavelengths of infrared light in order to increase the image quality.

Therefore, in order to usefully apply the dyes industrially, it has been continuously required to develop novel dyes that have excellent optical and pH stability, have a narrow absorption/emission wavelength range in a specific wavelength range, and exhibit a high molar absorption coefficient.

The above-described technical configuration is the background art for helping in the understanding of the present disclosure, and does not mean a conventional technology widely known in the art to which the present disclosure pertains.

SUMMARY OF THE INVENTION

An object of the present invention is to provide a fluorescent compound, a preparation method of the compound or a fluorescent diagnostic composition including the compound capable of being used as a contrast medium composition by improving further the fluorescent intensity in a florescent region of 400 to 900 nm while having excellent optical and pH stability and a narrow absorption/emission wavelength range, and particularly, improving the fluorescence by introducing a linker having a triazine structure substituted with a hydroxyl group to a cyanine-based fluorescent compound.

In order to solve the above-described problems, the inventors of the present application have developed a fluorescent compound represented by the following Chemical Formula 1.

[Chemical Formula 1]

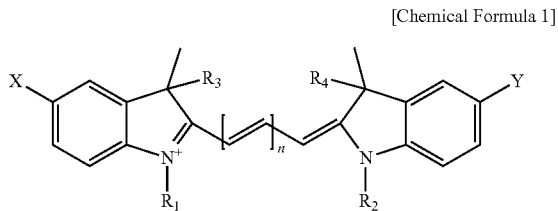

In Chemical Formula 1 above,

X and Y are the same as or different from each other, and each independently selected from H, $-SO_3^-$ and $SO_3H$, $R_1$ and $R_2$ are the same as each other or each independently selected from $C_{1-7}$ alkyl, $C_{8-18}$ alkyl, $-(CH_2)_mSO_3^-$, $-(CH_2)_mSO_3H$, and

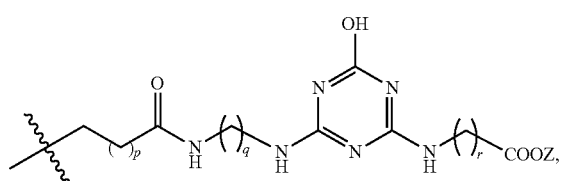

$R_3$ and $R_4$ are the same as or different from each other and each independently selected from $C_{1-7}$ alkyl, $-(CH_2)_mCOOZ$ and

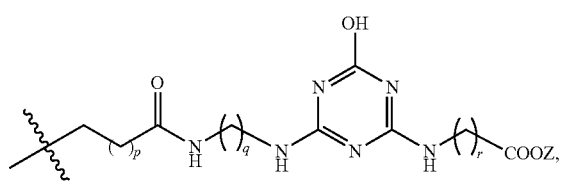

$R_3$ and $R_4$ are simultaneously not any one selected from $-(CH_2)_mCOOZ$ and

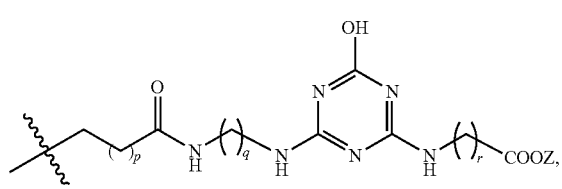

wherein,
n is an integer of 0 to 6,
m is an integer of 1 to 7,
p is an integer of 1 to 10,
q is an integer of 0 to 10,
r is an integer of 1 to 10, and
Z is selected from H, an N-succinimidol group, a hydrazinyl group, an N-hydroxysuccinimidyl group, an N-hydroxysuccinimidyl oxy group, a sulfosuccinimidyl oxy, a 4-sulfo-2,3,4,5-tetrafluoro phenyl group, a maleicimide $C_{0-10}$ alkylamyl group, a vinylsulfonyl group, a vinylsulfonyl $C_{0-6}$ alkylaminyl group and an amino $C_{0-6}$ alkyl.

According to exemplary embodiments of the present invention, the fluorescent compound has high stability under a water-soluble condition to be easily stored for a long time and improve pH stability, and particularly, can be more efficiently used for labeling and dyeing of a target material by introducing the triazine substituted with a hydroxyl group as a linker to improve the fluorescent intensity even at a low concentration as compared with the conventional structure. Further, the fluorescent compound is excellent in optical stability and exhibits stable fluorescence in long-term dyeing, and is excellent in fluorescence intensity while being not accumulated in the body, and thus, can be easily dyed and imaged in vivo even in the use of a small amount as compared with the conventional dyes to be economically used.

BRIEF DESCRIPTION OF THE DRAWINGS

The above and other aspects, features and other advantages of the present invention will be more clearly understood from the following detailed description taken in conjunction with the accompanying drawings, in which.

DETAILED DESCRIPTION OF THE PREFERRED EMBODIMENT

Figures 1, 2:
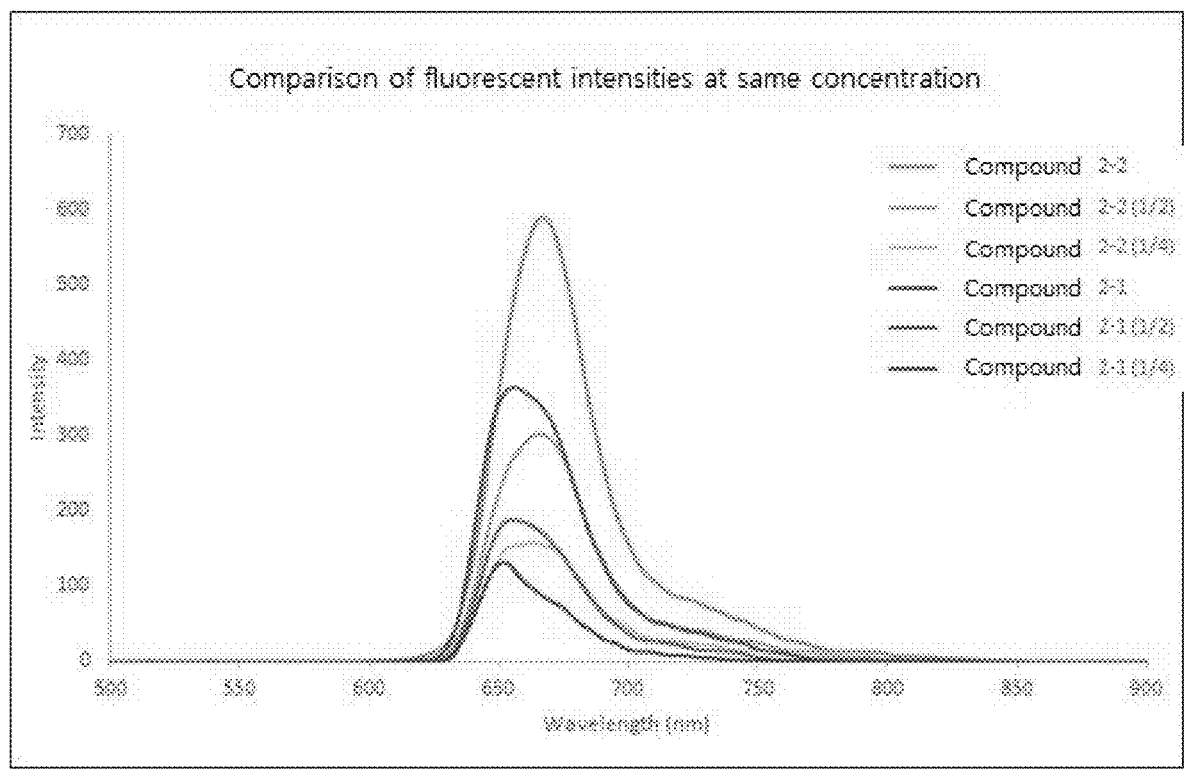
FIG. 1 is a graph showing a comparison result of fluorescent intensities of a compound in accordance with exemplary embodiments of the present invention and a conventional compound.
FIG. 2 is a table showing a comparison result of fluorescent intensities of a compound in accordance with exemplary embodiments of the present invention and a conventional compound using numerical values.

A fluorescent compound in accordance with exemplary embodiments of the present invention is invented to improve that a fluorescent compound including triazine substituted with chlorine which has been used in the related art has more noise and low fluorescent efficiency, wherein instead of the triazine substituted with chlorine, triazine substituted with a hydroxyl group is introduced as a linker of the cyanine-based compound.

Hereinafter, preparation methods of a fluorescent compound and a surfactant compound in accordance with exemplary embodiments of the present invention and the fluorescence efficiency of the composition in accordance with exemplary embodiments of the present invention will be described in detail by using embodiments of the present invention.

Hereinafter, the present invention will be described in more detail through Examples of the present invention. However, the following Examples are not to limit the scope of the present invention and will be described to help in the understanding of the present invention.

Exemplary embodiments of the present invention may use a fluorescent compound represented by the following Chemical Formula 1.

[Chemical Formula 1]

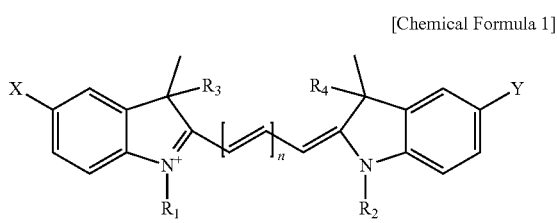

In Chemical Formula 1 above,

X and Y are the same as or different from each other, and each independently selected from H, —$SO_3^-$ and $SO_3H$, $R_1$ and $R_2$ are the same as each other or each independently selected from $C_{1-7}$ alkyl, $C_{8-18}$ alkyl, —$(CH_2)_m SO_3^-$, —$(CH_2)_m SO_3 H$, and

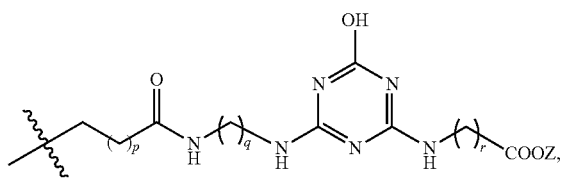

$R_3$ and $R_4$ are the same as or different from each other and each independently selected from $C_{1-7}$ alkyl, —$(CH_2)_m COOZ$ and

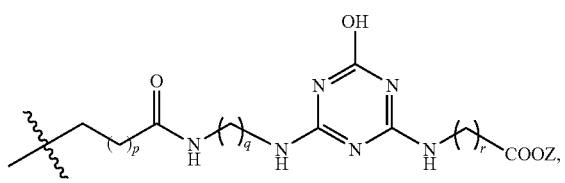

$R_3$ and $R_4$ are simultaneously not any one selected from —$(CH_2)_m COOZ$ and

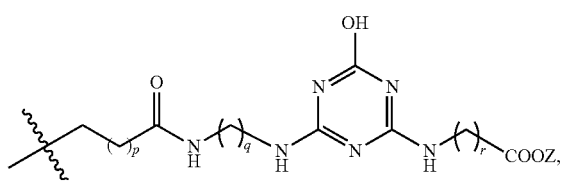

wherein, n is an integer of 0 to 6, m is an integer of 1 to 7, p is an integer of 1 to 10, q is an integer of 0 to 10, r is an integer of 1 to 10, and Z is selected from H, an N-succinimidol group, a hydrazinyl group, an N-hydroxysuccinimidyl group, an N-hydroxysuccinimidyl oxy group, a sulfosuccinimidyl oxy, a 4-sulfo-2,3,4,5-tetrafluoro phenyl group, a maleicimide $C_{0-10}$ alkylamyl group, a vinylsulfonyl group, a vinylsulfonyl $C_{0-6}$ alkylaminyl group and an amino $C_{0-6}$ alkyl.

The compound of Chemical Formula 1 provided in exemplary embodiments of the present invention may be useful to detect the biomaterial by labeling the biomaterial, and the biomaterial may be selected from the group consisting of proteins, peptides, carbohydrates, sugars, fats, antibodies, proteoglycan, glycoprotein, and siRNA.

Further, when labeling the biomaterial, the fluorescent compound provided in exemplary embodiments of the present invention binds to at least one functional group selected from an amine group, a hydroxyl group, and a thiol group in the biomaterial to label the biomaterial.

The method for labeling the fluorescent compound represented by Chemical Formula 1 is performed by using a buffer selected from the group consisting of a phosphate buffer, a carbonate buffer, and a tris buffer, an organic solvent selected from the group consisting of dimethyl sulfoxide, dimethylformamide, methanol, ethanol and acetonitrile, or water as a solvent and reacting the biomaterial, nanoparticles, or organic compounds with the compound of Chemical Formula 1 at pH 5 to 12. The reaction is sufficient for 30 minutes to 48 hours at a temperature of 20° C. to 80° C.

Most of biomaterials are dissolved in a predetermined buffer from a packaging unit, and in many cases, a separate buffer or pH is required to secure the stability of the biomaterials, and as a result, it is not easy to adjust the buffer or pH with a variable. The compound of Chemical Formula 1 according to exemplary embodiments of the present invention reacts with proteins in various buffers, reaction temperatures, and pH conditions to express fluorescence and thus is suitable to be used for labeling the biomaterials.

A preparation method of the compounds included in Chemical Formula 1 will be described.

Example 1: Synthesis of Initial Compound for Preparing Compounds in Accordance with Exemplary Embodiments of Present Invention (1) Synthesis of Compound 3-1

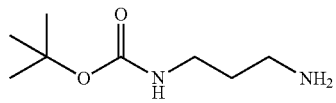

3-1

1,3-diaminopropane (20 g, 270 mmol, 7.96 eq) was dissolved in 70 ml of 1,4-dioxane. Di-tert-butyl dicarbonate (7.4 g, 33.9 mmol, 1 eq) was dissolved in 70 ml of 1,4-dioxane and then trickled in a 1,3-diaminopropane solution, and stirred at room temperature day and night and then dried under reduced pressure. The dried material was dissolved in distilled water and then filtered to extract the obtained filtrate with methylene chloride three times. An organic layer obtained after extraction was dried under reduced pressure to obtain a compound 3-1. (6 g, 91.5%)

$R_f$=0.4 (Silicagel, methylene chloride:methanol=8:1)

(2) Synthesis of Compound 3-2

3-2

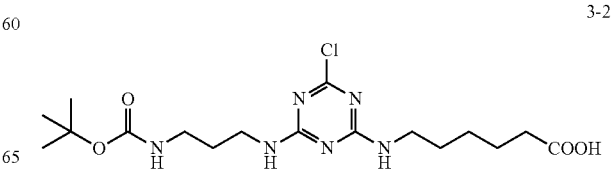

A compound 3-1 (5.1 g, 29.27 mmol, 1 eq) was dissolved in a mixed solution of 150 ml of acetone and 50 ml of distilled water and then stored at 4° C. or less. Cyanuric chloride (CNC) (5.4 g, 29.27 mmol, 1 eq) was fully dissolved in 150 ml of acetone and then added with 50 g of ice and dispersed at 4° C. or less. The compound 3-1 solution was trickled in a CNC solution, and then trickled in an aqueous solution of sodium hydrogencarbonate (fully dissolving 2.46 g carbonate in 50 ml of distilled water) and then, the reaction was performed at 4° C. or less for 2 hours. 6-aminohexanoic acid (1.42 g, 29.27 mmol, 1 eq) was dissolved in 50 ml of distilled water and then trickled in the reaction solution. The aqueous solution of sodium hydrogencarbonate was trickled and the reaction was performed at room temperature for 2 hours and then stirred at 4° C. day and night. The reaction solution was dried under reduced pressure and purified using silica gel chromatography to obtain a compound 3-2. (9 g, 73.8%)

$R_f$=0.7 (Silicagel, methylene chloride:methanol=8:1)

LC/MS, calculated value of $C_{17}H_{29}ClN_6O_4$ 416.91, measured value of 415.2

(3) Synthesis of Compound 3-3

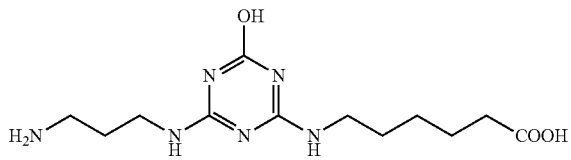

3-3

A compound 3-2 (3 g, 7.2 mmol, 1 eq) was fully dissolved in 40 ml of acetonitrile (ACN) and then added with 40 ml of distilled water. Thereafter, 20 ml of a 6 N aqueous hydrochloric acid solution was added, and then stirred at 60° C. day and night. The reaction solution was dried under reduced pressure and subjected to a reverse phase column to obtain a compound 3-3. (1.5 g, 69.8%)

$R_f$=0.4 (Silicagel, methylene chloride:methanol=8:1)

LC/MS, calculated value of $C_{12}H_{22}N_6O_3$ 298.35, measured value of 297.3

Example 2: Synthesis of Initial Compound 1-1 for Preparing Compounds in Accordance with Exemplary Embodiments of the Present Invention (1) Synthesis of Compound 4-1

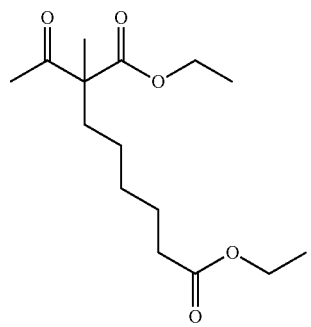

4-1

Ethyl 2-methyl acetoacetate (29.2 ml, 0.203 mol, 1 eq), a 21% sodium ethoride solution (64 ml, 0.816 mol, 4 eq), ethyl 6-bromohexanoate (34 ml, 0.192 mol, 1 eq), and ethanol (200 ml) were added and then refluxed at 120° C. for 12 hours. Thereafter, the solvent was extracted by neutralizing pH using 1 M hydrochloric acid and then using chloroform and distilled water. The extracted solvent was dried under reduced pressure and purified using normal chromatography to obtain a compound 4-1. (36.8 g, 63.4%)

$R_f$=0.34 (Silicagel, Hexane/ethyl acetate=10:1 v/v)

(2) Synthesis of Compound 4-2

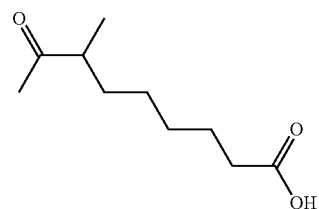

4-2

Sodium hydroxide (6.2 g, 0.170 mol, 3.5 eq), methanol (47.2 ml), and distilled water (15.6 ml) were added to the compound 4-1 (13.7 g, 0.0486 mol, 1 eq) and then refluxed at 50° C. for 12 hours. Thereafter, the solvent was dried under reduced pressure and then extracted by adjusting pH to 1 using 1 M hydrochloric acid and using ethyl acetate, and then dried under reduced pressure to obtain a compound 4-2. (8.17 g, 90.7%)

$R_f$=0.05 (Silicagel, Hexane/ethyl acetate=10:1 v/v)

(3) Synthesis of Compound 4-3

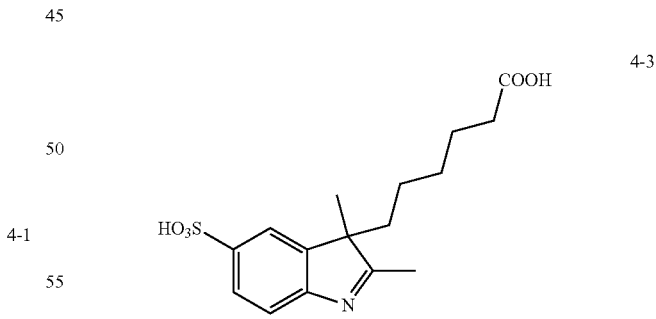

4-3 p-hydrazinobenzensulfonic acid hemihydrate (8.25 g, 0.0438 mol, 1 eq) and acetic acid were added to the compound 4-2 (8.165 g, 0.0438 mol, 1 eq) and then refluxed at 120° C. for 5 hours. The mixture was dried under reduced pressure and then purified using normal chromatography and dried under reduced pressure to obtain a compound 4-3. (12.6 g, 84.8%)

$R_f$=0.51 (Silicagel, isobutanol/n-propanol/ethyl acetate/water 2:4:1:3 v/v/v/v)

(4) Synthesis of Compound 4-4

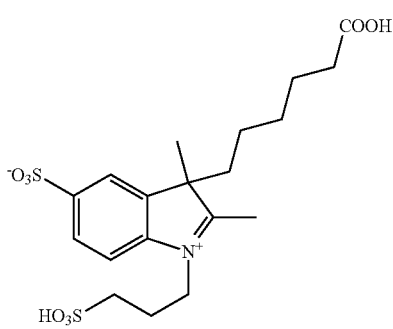

4-4

Sodium acetic acid (4.16 g, 0.061 mol, 1.65 eq), 1,3-propane sultone (21.3 ml, 0.243 mol, 6.57 eq), and acetonitrile (24.8 ml) were added to the compound 4-3 (12.57 g, 0.037 mol, 1 eq) and then refluxed at 110° C. for 5 hours. Thereafter, the mixture was dried under reduced pressure and then purified using reverse phase chromatography and dried under reduced pressure to obtain a compound 4-4. (12 g, 70.6%)

$R_f$=0.3 (Silicagel, isobutanol/n-propanol/ethyl acetate/water 2:4:1:3 v/v/v/v)

(5) Synthesis of Compound 4-5

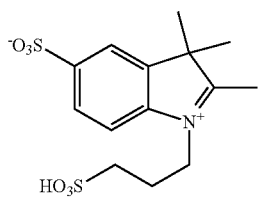

4-5

Sodium acetate (17.87 g, 0.216 mol, 1.2 eq), 1,3-propane sultone (70.5 ml, 0.8 mol, 4.5 eq), and acetonitrile (42 ml) were added to the compound 4-1 (50 g, 0.18 mol, 1 eq). Thereafter, the mixture was refluxed at 110° C. for 12 hours and then particles were captured using ethyl acetate and dried to obtain a compound 4-5. (61 g, 94%)

$R_f$=0.3 (Silicagel, isobutanol/n-propanol/ethyl acetate/water 2:4:1:3 v/v/v/v)

(6) Synthesis of Compound 4-6

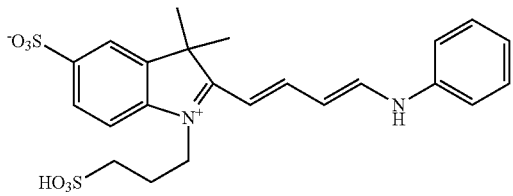

4-6

Malonaldehyde dianilide hydrochloride (42.9 g, 0.166 mol, 1 eq), triethylamine (2.3 ml, 0.016 mol, 0.1 eq), and acetic acid (551 ml) were added to the compound 4-5 (60 g, 0.166 mol, 1 eq) and then heated and refluxed at 140° C. Thereafter, the particles were precipitated using ethyl acetate and then dried. The compound was purified using normal chromatography and then dried under reduced pressure to obtain a compound 4-6. (7.5 g, 8.5%)

$R_f$=0.55 (Silicagel, isobutanol/n-propanol/ethyl acetate/water 2:4:1:3 v/v/v/v)

(7) Synthesis of Compound 1-1

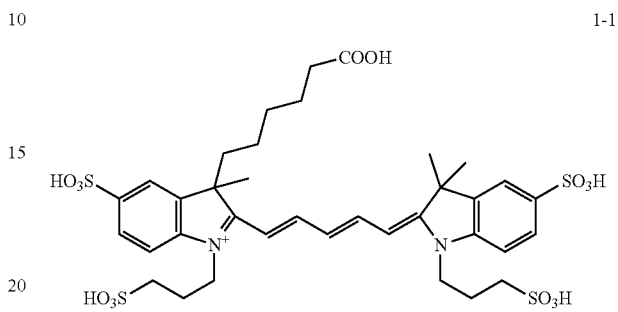

1-1

The compound 4-4 (6.5 g, 0.014 mol, 1 eq) and the compound 4-6 (7.5 g, 0.014 mol, 1 eq) were added to a mixed solution of triethylamine (16.6 ml, 0.12 mol, 8.5 eq), anhydrous acetic acid (7.3 ml), and DMF (75 ml) and then reacted at room temperature for 1 hour. Thereafter, the particles were precipitated using ethyl acetate and then dried. The compound was purified using normal chromatography and then dried under reduced pressure to obtain a compound 1-1. (250 mg, 2%)

$R_f$=0.4 (Silicagel, isobutanol/n-propanol/ethyl acetate/water 2:4:1:3 v/v/v/v)

LC/MS, calculated value of $C_{36}H_{44}N_2Na_2O_{14}S_4$ 902.98, measured value of 901

Example 3: Synthesis of Compound 1-2 as Compound in Accordance with Exemplary Embodiments of the Present Invention

(1) Synthesis of Compound 2-1

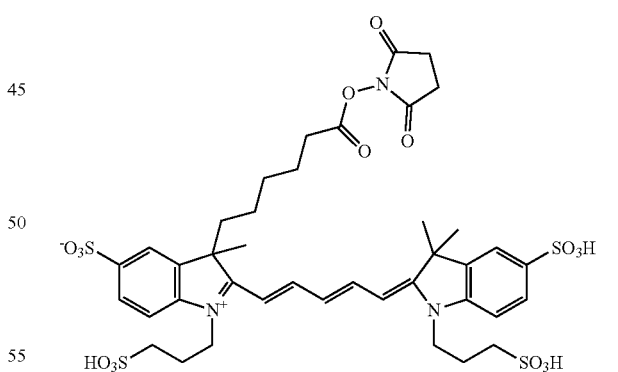

2-1

The compound 1-1 (100 mg, 0.1165 mmol, 1 eq), TSTU (77 mg, 0.2563 mmol, 2.2 eq), and triethylamine (125 µl, 0.897 mmol, 7.7 eq) were added to 10 mL of DMF and reacted at room temperature for 40 minutes. Solid particles generated after reaction were filtered. The solid particles were washed with ethyl acetate 2 to 3 times to obtain a compound 2-1. (111 mg, 100%)

$R_f$=0.44 (Silicagel, isobutanol/n-propanol/ethyl acetate/water 2:4:1:3 v/v/v/v)

LC/MS, calculated value of $C_{40}H_{49}N_3O_{16}S_4$ 956.09, measured value of 954

(2) Synthesis of Compound 1-2

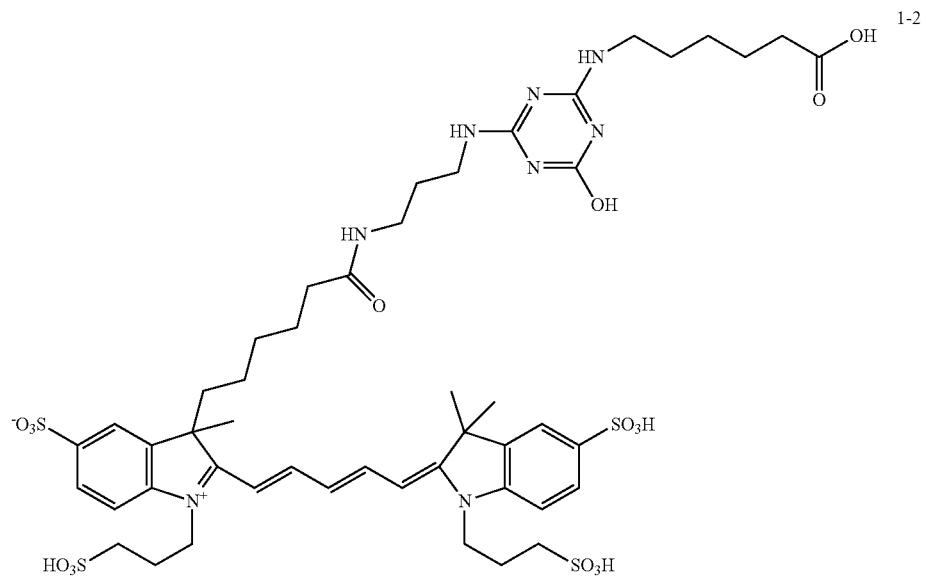

The compound 2-1 (93 mg, 97.1 umol, 1 eq) was fully dissolved in 10 mL of DMF. The compound 3-3 (44 mg, 1546 umol, 1.5 eq) was fully dissolved in 1 ml of DMF and then added to a compound 2-1 solution and then added with Wheeinig base (125 μl, 10 eq) and stirred for a day and night at room temperature. After the reaction was confirmed, particles were produced by adding ether and filtered and dried. The obtained material was purified using reverse phase chromatography and then dried under reduced pressure to obtain a compound 1-2. (95 mg, 85.9%)

$R_f$=0.35 (Silicagel, isobutanol/n-propanol/ethyl acetate/water 2:4:1:3 v/v/v/v)

LC/MS, calculated value of $C_{45}H_{66}N_8O_{16}S_4$ 1139.34, measured value of 1138.2

Example 4: Another Synthesis Method of Compound 1-2 as Compound in Accordance with Exemplary Embodiments of the Present Invention (1) Synthesis of Compound 1-3

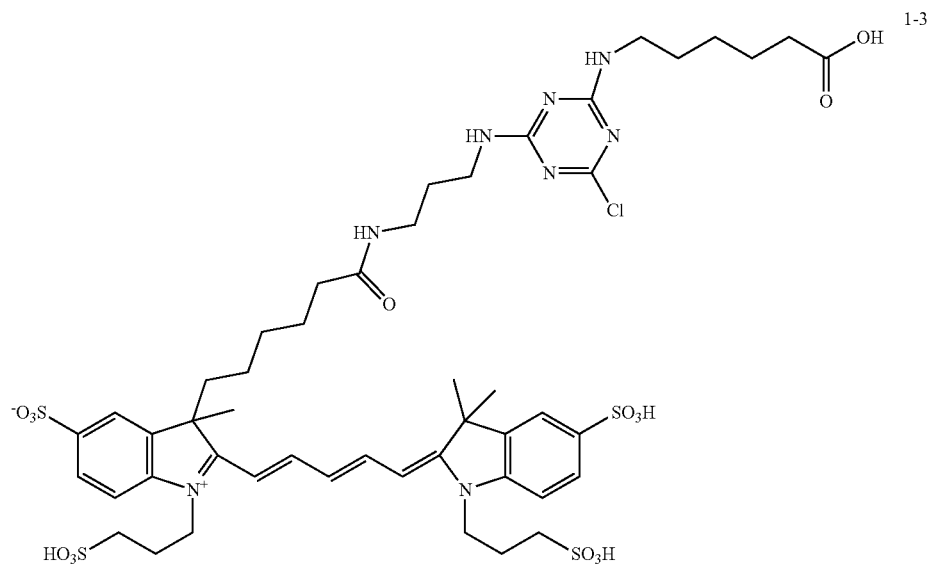

The compound 2-1 (553 mg, 580 umol, 1 eq) was fully dissolved in 20 mL of DMF. The compound 3-2 (724 mg, 1.74 mmol, 3 eq) was fully dissolved in 36 mL of a HCl solution (4 M in dioxane), stirred for 1 hour, and then dried under reduced pressure and the obtained material was added to 20 mL of DMF and then fully dissolved. The compound 3-2 was added to the compound 2-1 solution and then added with Wheeinig base (505 μl, 5 eq) and stirred at room temperature for 1 hour. After the reaction was confirmed, particles were produced by adding ether and filtered and dried. The obtained material was purified using reverse phase chromatography and then dried under reduced pressure to obtain a compound 1-3. (490 mg, 73.0%)

$R_f$=0.34 (Silicagel, isobutanol/n-propanol/ethyl acetate/water 2:4:1:3 v/v/v/v)

LC/MS, calculated value of $C_{48}H_{65}ClN_8O_{15}S_4$ 1157.79, measured value of 1153.8

(2) Another Synthesis Method of Compound 1-2

10 mL of ACN and 10 mL of distilled water were added in the compound 1-3 (200 mg, 173 umol, 1 eq), respectively, and fully dissolved. Thereafter, 5 mL of a 6 N aqueous hydrochloric acid solution was added, and then stirred at 60° C. for a day and night. The reaction solution was freeze-dried and subjected to a reverse phase column to obtain a compound 1-2. (122 mg, 61.9%)

$R_f$=0.34 (Silicagel, isobutanol/n-propanol/ethyl acetate/water 2:4:1:3 v/v/v/v)

LC/MS, calculated value of $C_{48}H_{65}ClN_8O_{15}S_4$ 1157.79, measured value of 1153.8

Example 5: Synthesis of Compound 2-2 as Compound in Accordance with Exemplary Embodiments of the Present Invention

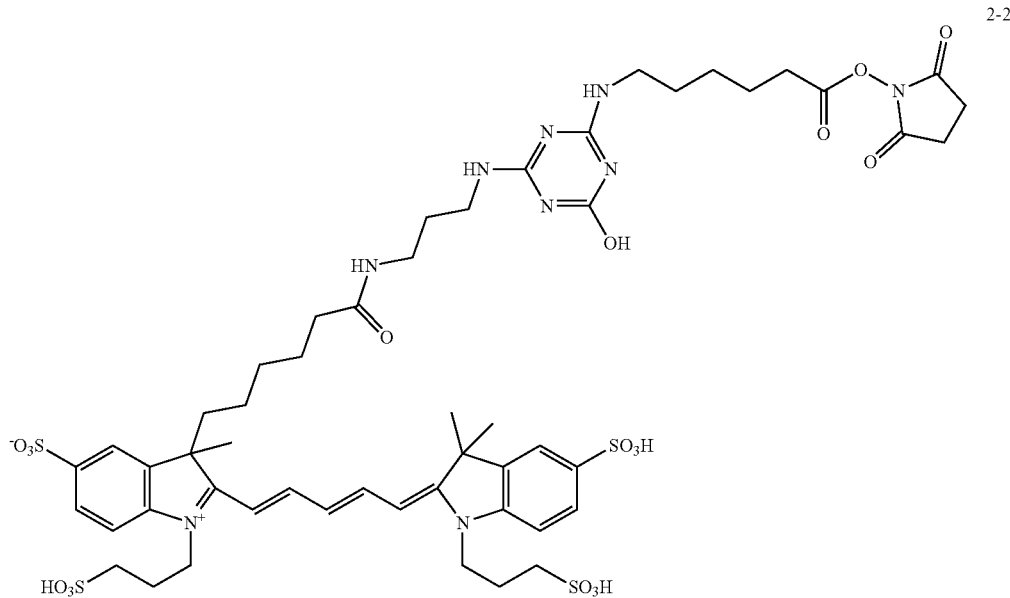

The compound 2-1 (100 mg, 0.088 mmol, 1 eq), TSTU (53 mg, 0.2563 mmol, 2 eq), and triethylamine (27 mg, 0.263 mmol, 3 eq) were added to 10 mL of DMF and then reacted at room temperature for 40 minutes. Solid particles generated after reaction were filtered. The solid particles were washed with ethyl acetate 2 to 3 times to obtain a compound 2-2. (80 mg, 73.6%)

Rf=0.40 (Silicagel, isobutanol/n-propanol/ethyl acetate/water 2:4:1:3 v/v/v/v)

LC/MS, calculated value of $C_{52}H_{69}N_9O_{18}S_4$ 1236.41, measured value of 1234.0

Examples 6 to 10: Synthesis of Compounds 1-4, 1-5, 1-6, 1-7 and 1-8 as Compounds in Accordance with Exemplary Embodiments of the Present Invention As the similar manner as described in Examples 1 to 5, Examples 6 to 10 were conducted.

Example 6. Synthesis of Compound 1-4
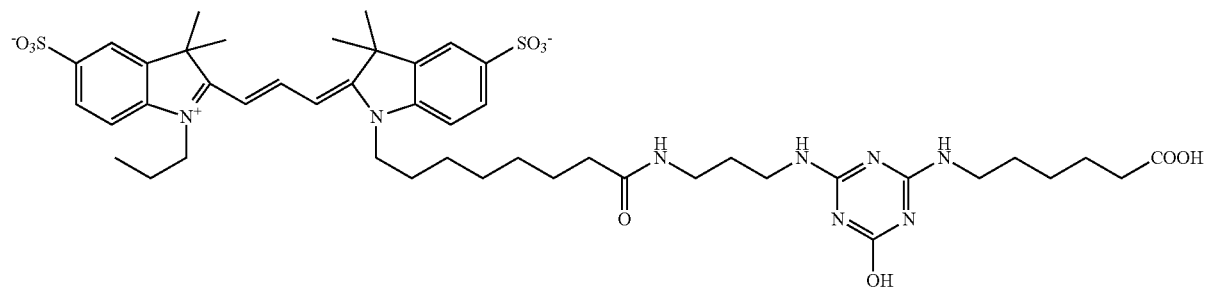
1-4
(110 mg, 80.9%)
$R_f$=0.5 (Silicagel, acetonitrile/water=3:1 v/v)
Example 7. Synthesis of Compound 1-5
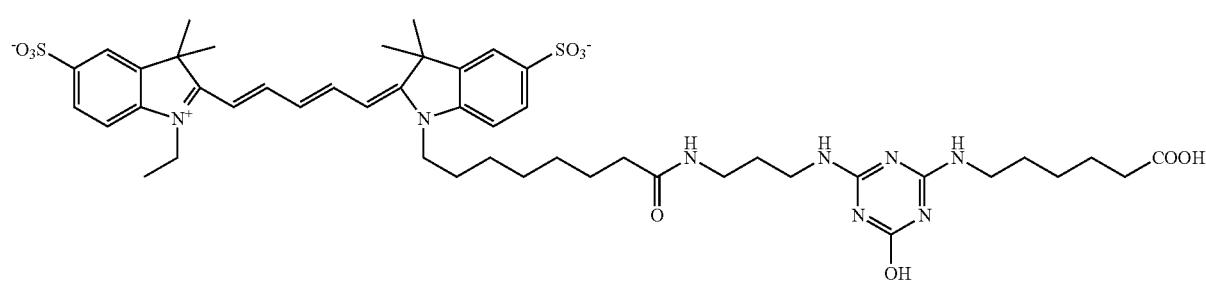
1-5
(105 mg, 83.5%)
$R_f$=0.45 (Silicagel, acetonitrile/water=3:1 v/v)
Example 8. Synthesis of Compound 1-6
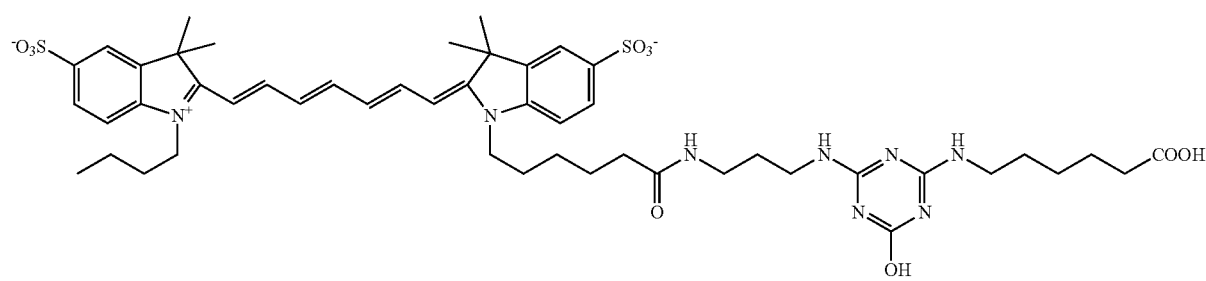
1-6
(90 mg, 71.0%)
$R_f$=0.4 (Silicagel, acetonitrile/water=3:1 v/v)

Example 9. Synthesis of Compound 1-7

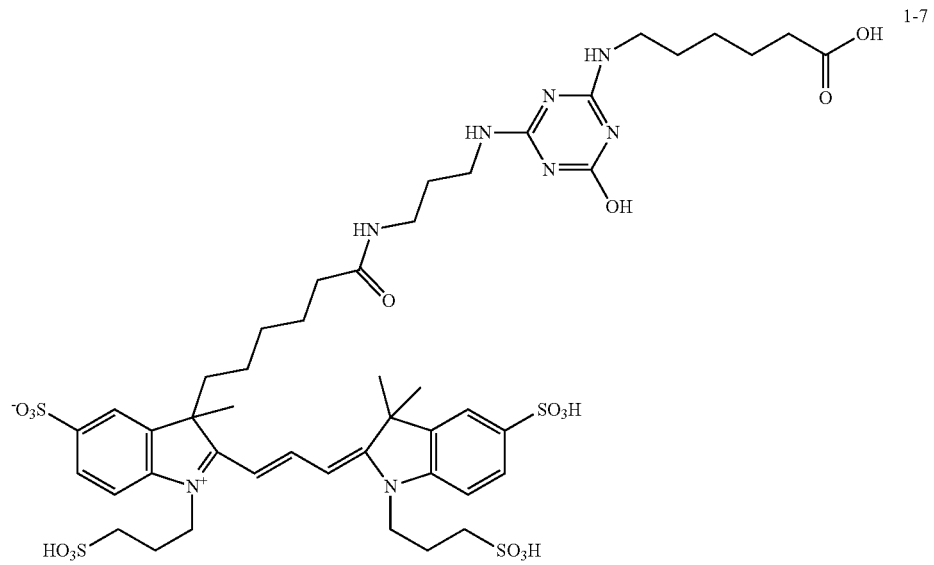

(92 mg, 90.3%)
R$_f$=0.6 (Silicagel, acetonitrile/water=3:1 v/v)

Example 10. Synthesis of Compound 1-8

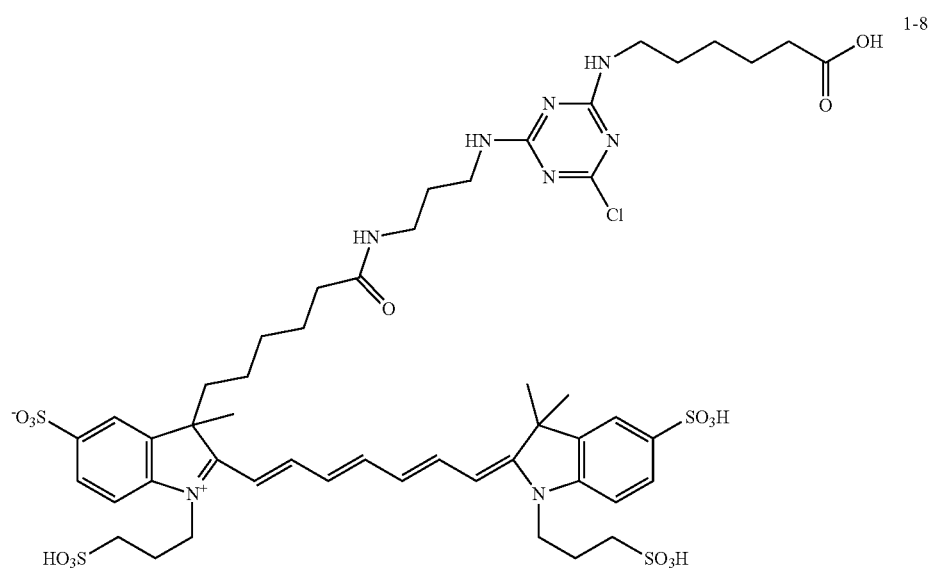

(53 mg, 70.5%)
R$_f$=0.5 (Silicagel, acetonitrile/water=3:1 v/v)

Fluorescent values at the same absorption wavelength of the compound 2-2 included in the compounds of exemplary embodiments of the present invention and the compound 2-1 not included in the compounds of exemplary embodiments of the present invention were compared through Comparative Examples.

Comparative Example 1. Comparison of Fluorescent Values at the Same Absorption Wavelength of Compound 2-1 and Compound 2-2

In order to confirm an increase in fluorescent intensity by introducing triazine substituted with a hydroxyl group shown in the compound 3-3 as a linker, the following comparative experiment was conducted.

The compound 2-1 was dissolved in DMF at a concentration of 10 mg/ml and then 5 μl of the compound 2-1 was added to 5 ml of PBS at room temperature, and 5 μl of the compound 2-2 was added to 5 mL of PBS at the same concentration in the same manner. The absorption was measured by adding 2 mL of two samples by 1 mL of PBS and the fluorescence was measured even after diluting the compounds.

With respect to the compound 2-2, which corresponds to the compound 2-1 including a triazine structure substituted with a hydroxyl group of the compound 3-3, it was confirmed that in a single dye form, the higher the concentration, the higher the fluorescence intensity as compared to the compound 2-1.

In the case of introducing the triazine structure substituted with a hydroxyl group as a linker to the compound 2-1, at a concentration representing the same absorption intensity, the increase in fluorescence intensity of 162% or more was confirmed and illustrated in FIGS. 1 and 2.

In FIGS. 1 and 2, the numerical values of ½ and ¼ indicate that the initial concentration was diluted.

As described above, the fluorescent compound introducing the triazine substituted with the hydroxyl group provided in exemplary embodiments of the present invention has high fluorescence efficiency such as fluorescent intensity and the like as compared with the conventional fluorescent compound at the same concentration to accurately detect a target material even in a small amount of biomaterial.

The present invention is not limited by the above-described embodiments, and various modifications and changes can be made by those skilled in the art and may be used in various biological and chemical fields, and are included in the spirit and scope of the present invention as defined in the appended claims.

What is claimed is:

1. A fluorescent compound for labeling a biomaterial having the following Chemical Formula 1:

[Chemial Formula 1]

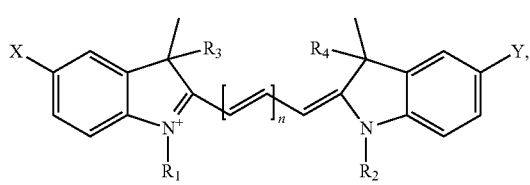

where X and Y are the same as or different from each other, and each independently selected from H, —SO$_3^-$ and SO$_3$H, $R_1$ and $R_2$ are independently selected from $C_{1-5}$ alkyl, —(CH$_2$)$_m$SO$_3^-$, —(CH$_2$)$_m$SO$_3$H, and

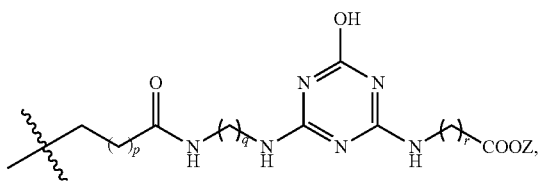

$R_3$ and $R_4$ are independently selected from $C_{1-5}$ alkyl, —(CH$_2$)$_m$COOZ and

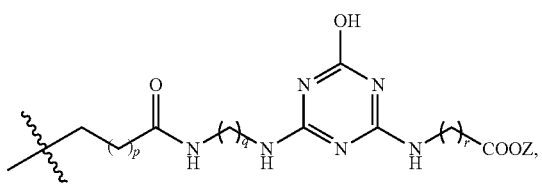

And among $R_1$, $R_2$, $R_3$, and $R_4$, only one is selected as

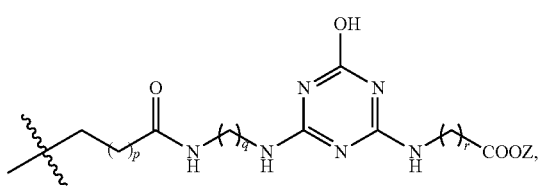

n is an integer of 2 to 4,
m is an integer of 2 to 4,
p is an integer of 2 to 5,
q is an integer of 2 to 5,
r is an integer of 2 to 5, and
Z is selected from H, an N-succinimidyl group, an N-hydroxysuccinimidyl group, and an N-hydroxysuccinimidyl oxy group.

2. The fluorescent compound of claim 1, wherein the compound of Chemical Formula 1 above is any one selected from compounds represented by the following Chemical Formulas 1-2
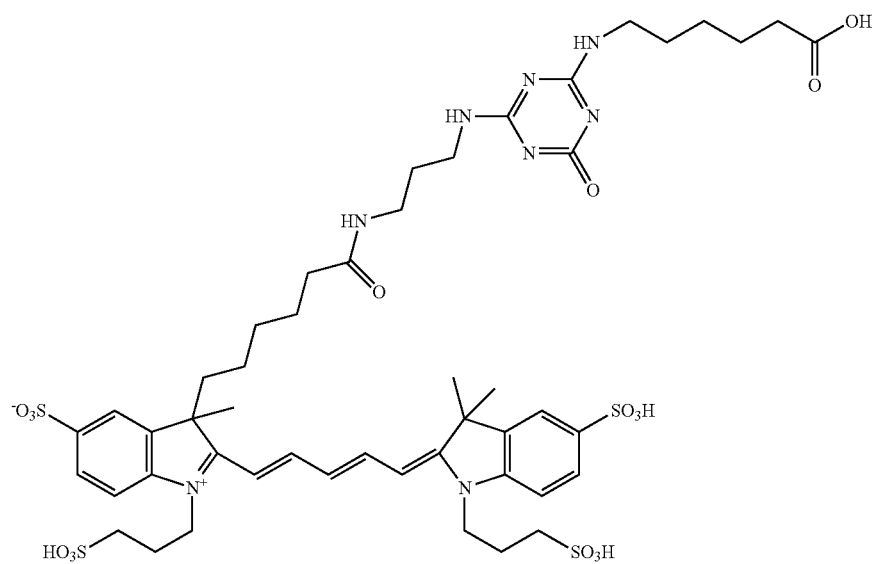
2-2
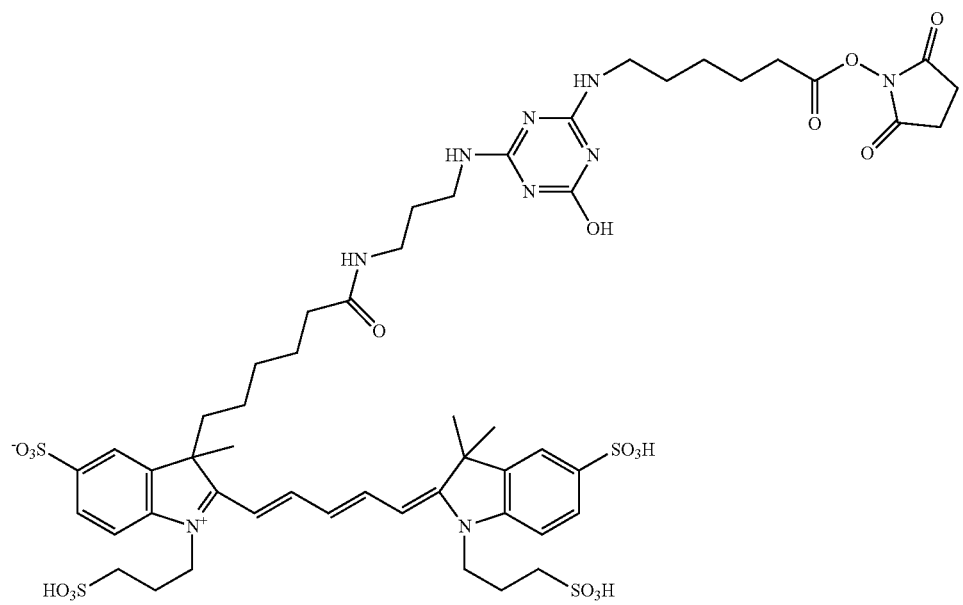
1-4
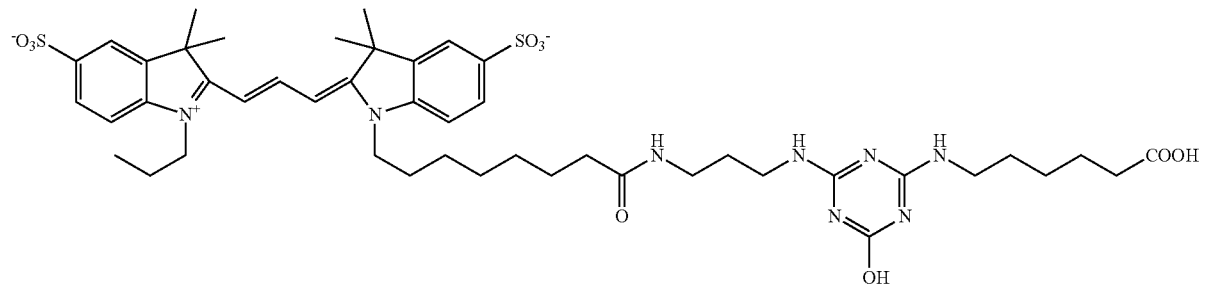

1-5
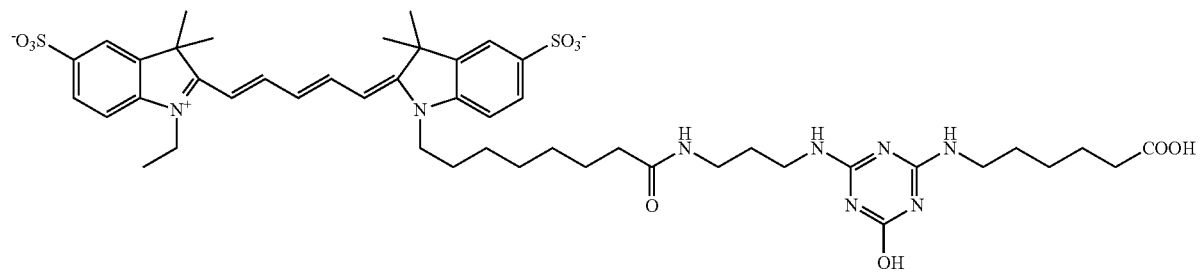
1-6
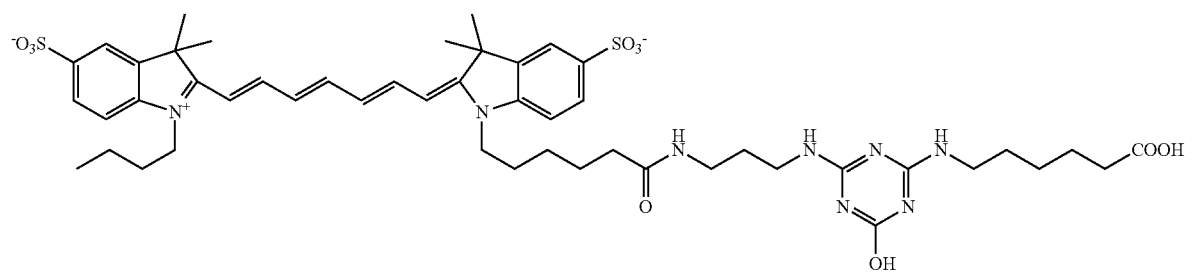
1-7
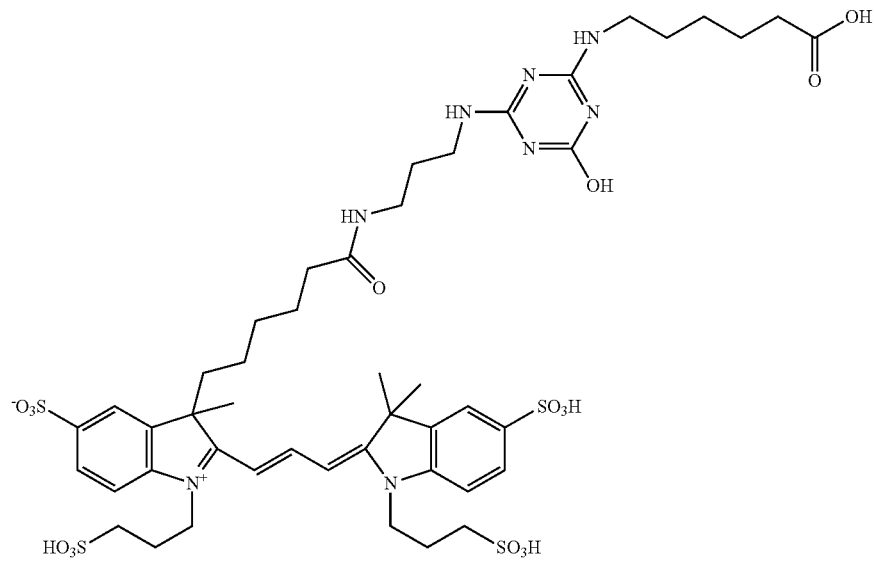

1-8

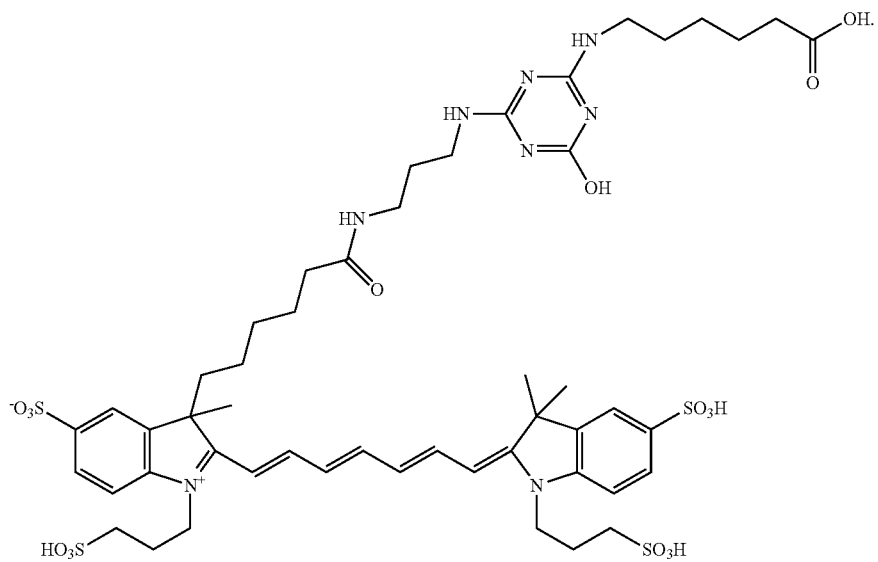

3. The fluorescent compound of claim 1, wherein the biomaterial is any one selected from the group consisting of proteins, peptides, carbohydrates, sugars, fats, antibodies, proteoglycan, glycoprotein, and siRNA.

4. A fluorescent diagnostic composition for detecting a biomaterial comprising a fluorescent compound represented by the following Chemical Formula 1:

[Chemical Formula 1]

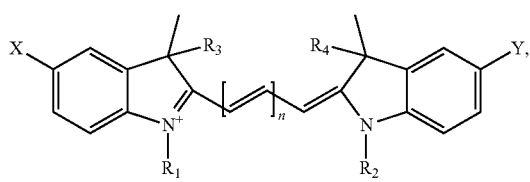

where X and Y are the same as or different from each other, and each independently selected from H, —SO$_3^-$ and SO$_3$H, R$_1$ and R$_2$ are independently selected from C$_{1-5}$ alkyl, —(CH$_2$)$_m$SO$_3^-$, —(CH$_2$)$_m$SO$_3$H, and

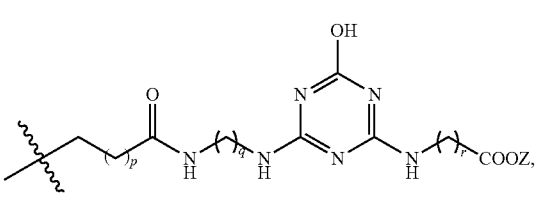

R$_3$ and R$_4$ are independently selected from C$_{1-5}$ alkyl, —(CH$_2$)$_m$COOZ and

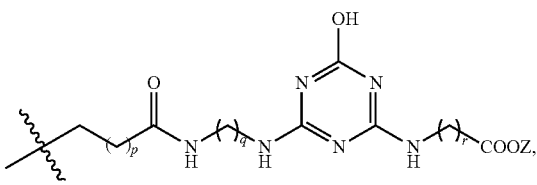

And among R$_1$, R$_2$, R$_3$, and R$_4$, only one is selected as

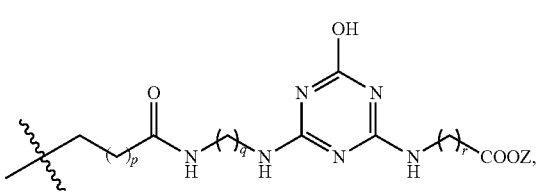

n is an integer of 2 to 4,
m is an integer of 2 to 4,
p is an integer of 2 to 5,
q is an integer of 2 to 5,
r is an integer of 2 to 5, and
Z is selected from H, an N-succinimidyl group, an N-hydroxysuccinimidyl group, and an N-hydroxysuccinimidyl oxy group.

5. The fluorescent diagnostic composition of claim 4, wherein the compound of Chemical Formula 1 above is any one selected from compounds represented by the following Chemical Formulas 1-2
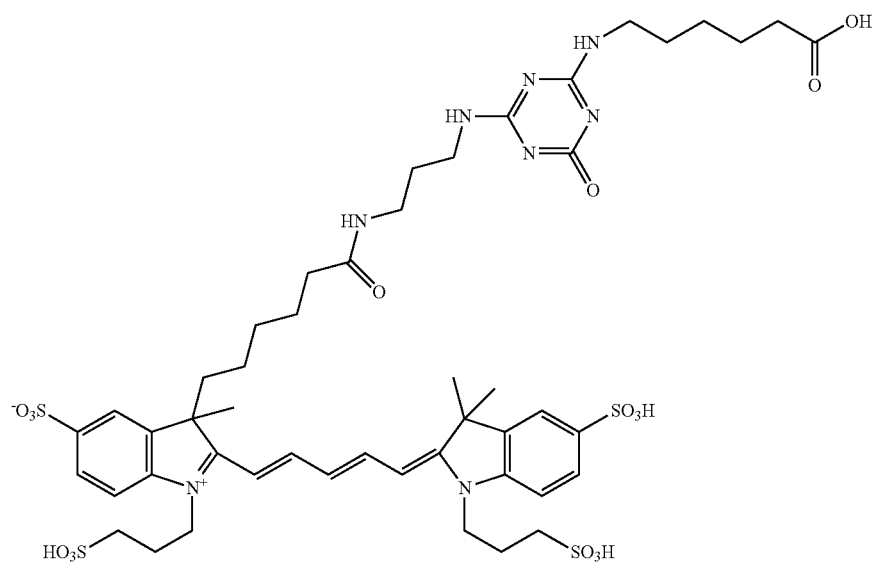
2-2
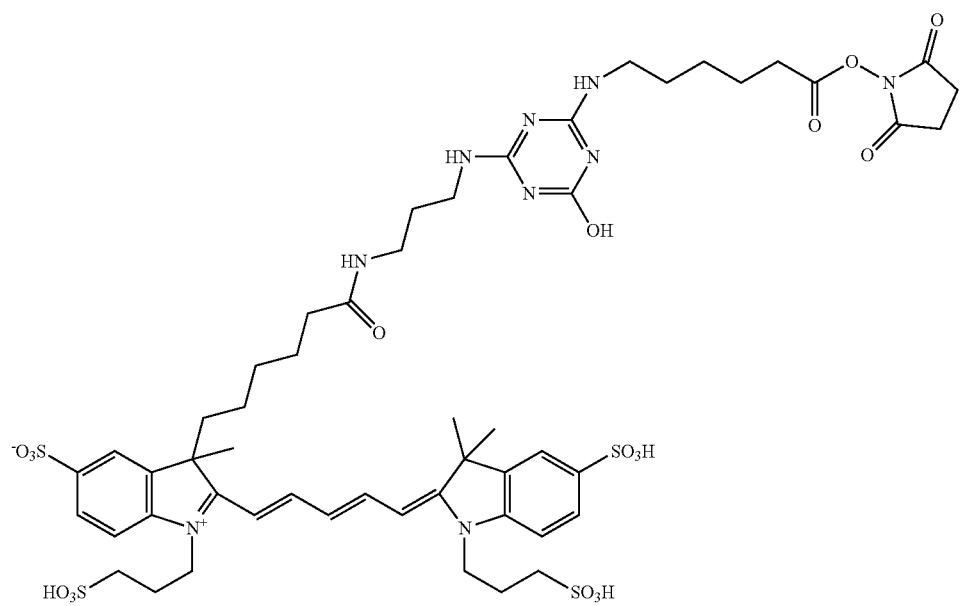
1-4
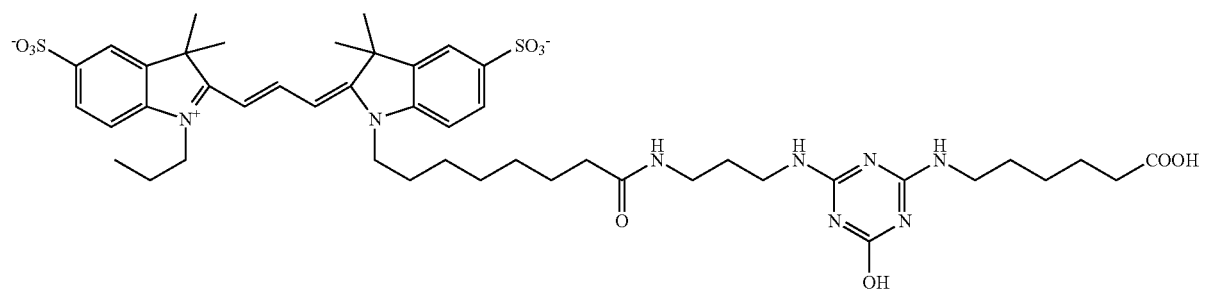

1-5
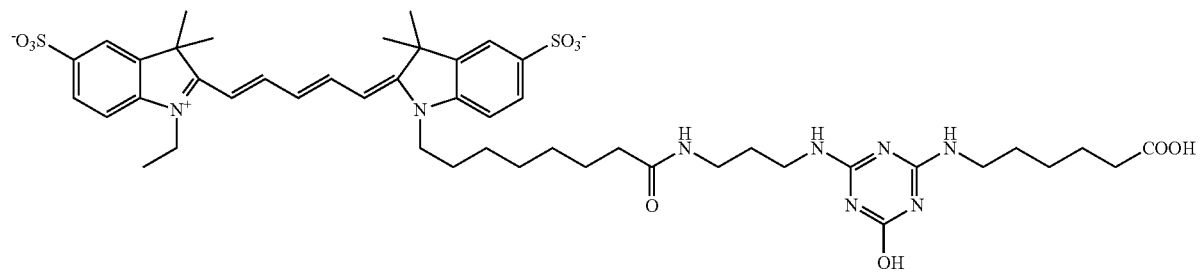
1-6
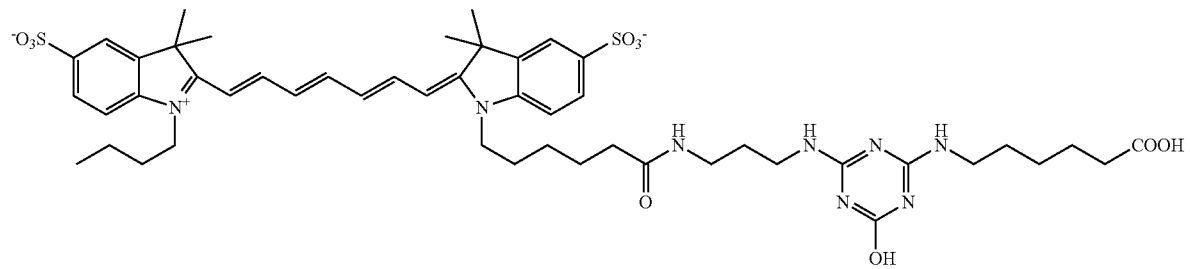
1-7
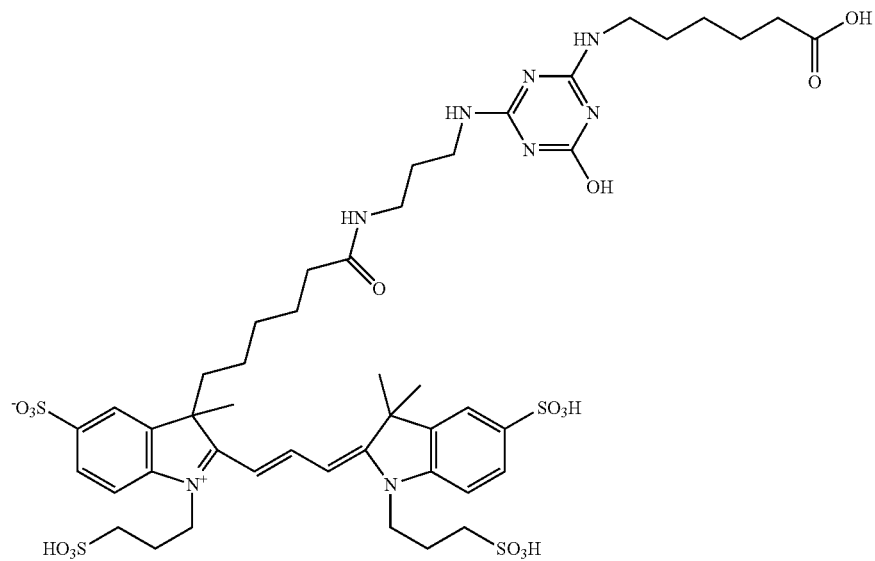

-continued
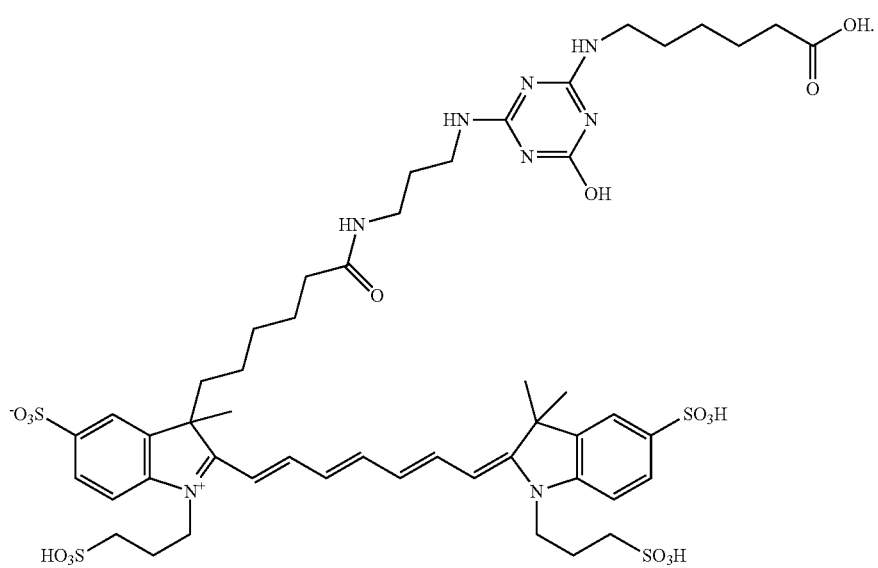
1-8
6. The fluorescent diagnostic composition of claim 4, wherein the biomaterial is any one selected from the group consisting of proteins, peptides, carbohydrates, sugars, fats, antibodies, proteoglycan, glycoprotein, and siRNA.
* * * * *